United States Patent
Yang et al.

(10) Patent No.: US 7,821,402 B2
(45) Date of Patent: Oct. 26, 2010

(54) IC TAGS/RFID TAGS FOR MAGNETIC RESONANCE IMAGING APPLICATIONS

(75) Inventors: Xiaoyu Yang, Indiana, PA (US); Hiroyuki Fujita, Highland Heights, OH (US); Tsinghua Zheng, Aurora, OH (US)

(73) Assignee: Quality ElectroDynamics, Mayfield Village, OH (US)

( * ) Notice: Subject to any disclaimer, the term of this patent is extended or adjusted under 35 U.S.C. 154(b) by 1145 days.

(21) Appl. No.: 11/418,471

(22) Filed: May 5, 2006

(65) Prior Publication Data

US 2007/0257800 A1 Nov. 8, 2007

(51) Int. Cl.
*G08B 13/14* (2006.01)

(52) U.S. Cl. ............... 340/572.8; 340/572.7; 340/572.5

(58) Field of Classification Search ............. 340/572.5, 340/572.1–572.4, 572.6–572.8; 343/841; 607/60

See application file for complete search history.

(56) References Cited

U.S. PATENT DOCUMENTS

| | | | |
|---|---|---|---|
| 7,359,173 B2* | 4/2008 | Biagi et al. | 361/104 |
| 7,388,498 B2* | 6/2008 | Spencer et al. | 340/572.5 |
| 2005/0206500 A1* | 9/2005 | Ferren et al. | 340/5.82 |
| 2006/0212096 A1* | 9/2006 | Stevenson | 607/60 |

* cited by examiner

*Primary Examiner*—Anh V La
(74) *Attorney, Agent, or Firm*—Nixon & Vanderhye P.C.

(57) ABSTRACT

An RFID tag for use with an MRI machine has an integrated circuit and structure for protecting it from damage when exposed to an intense MRI RF transmitter field. The structure for protecting the integrated circuit may include a controllable low impedance device coupled across the integrated circuit, a controllable high impedance device coupled in series with the integrated circuit, and/or frequency selective RF filter.

42 Claims, 9 Drawing Sheets

FIG. 13

IC TAGS/RFID TAGS FOR MAGNETIC RESONANCE IMAGING APPLICATIONS

BACKGROUND

1. Technical Field

Non-limiting, exemplary embodiments relate to a radio frequency identification (RFID) tag for use in an environment of a magnetic resonance imaging (MRI) machine. More particularly, non-limiting, exemplary embodiments relate to a protection device for an RFID tag in an MRI environment so that the RFID tag is not damaged or destroyed by the strong RF fields associated with MRI, and to an apparatus having an MRI machine and an associated RFID tag reading system.

2. Description of Related Art

RFID technology using parasitic RF receive/transmit circuits is widely used to automatically identify articles. RFID technology possesses numerous advantages over traditional identification technology. For example, because RFID technology uses an RF field to operate, no line of sight is required and because it is powered parasitically by received RF signals it requires no internal battery or other power supply. Also, an integrated circuit (IC) chip used in an RFID tag may possess a high memory capacity enabling RFID applications to satisfy more than mere identification purposes. Information stored in the IC chip of the RFID tag may be repeatedly and dynamically changed. The whole RFID tag can be enclosed inside a protective material since the RFID tag does not typically include moving parts. The RFID tag is therefore very robust and reliable. An information transfer process in an RFID tag system does not necessarily require human intervention. Finally, an RFID tag system is reasonably inexpensive. Due to these numerous advantages, RFID technology is used in a wide range of areas such as transportation ticketing, access control, animal identification, electronic immobilization, container identification, inventory control, sporting events and medical applications.

Figure 1:
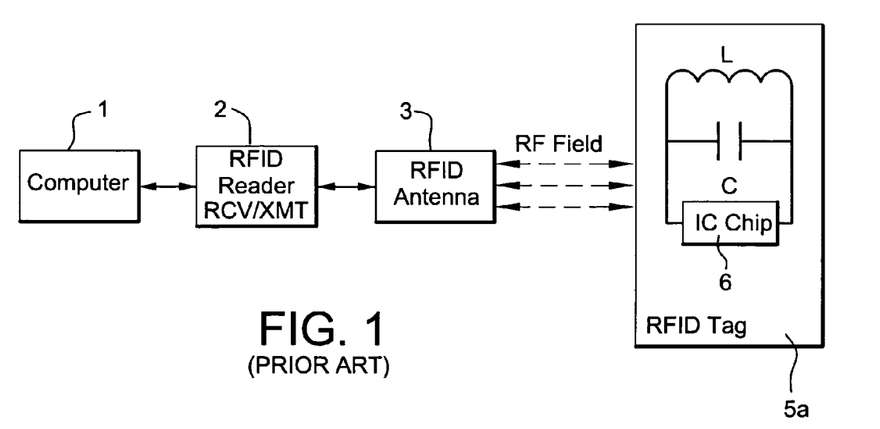
FIG. 1 is a schematic view of a known inductive coupling RFID tag system.

FIG. 1 shows a traditional inductively coupled RFID tag system including a computer 1, an RFID reader 2, an RFID antenna 3 and an RFID tag 5a. The computer 1 is operatively coupled to the RFID reader 2 and includes a memory for storing information. In addition to reading data from the RFID tag 5a (which typically involves two-way RF transmit/receive functions), the RFID "reader" 2 may also be used to perform programming processes. That is, the RFID reader 2 may be used to transmit and write information into a memory of the RFID tag 5a. The RFID tag 5a includes an IC chip 6, an antenna L, and capacitance C. The IC chip 6 provides control functions and a memory for storing data. The data stored in the memory of the IC chip 6 may include information such as inventory, device/product integrity and quality control information. Storing such information in the memory of the IC chip avoids the need for tracking this information with paper.

Figure 2:
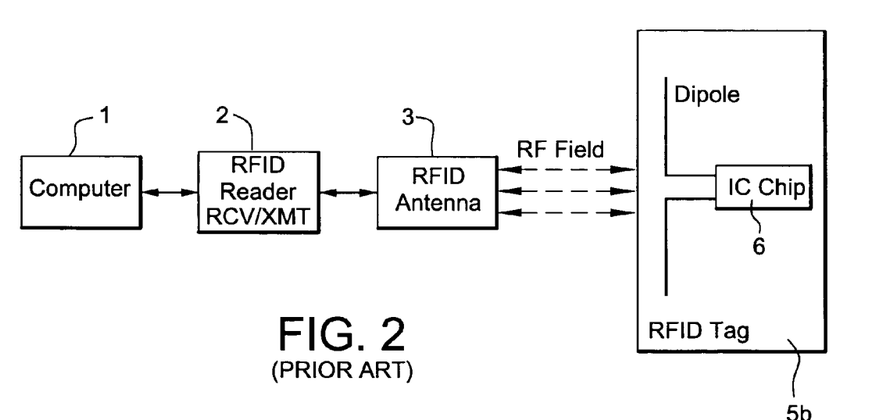
FIG. 2 is a schematic view of a known capacitive coupling RFID tag system.

FIG. 2 shows a traditional capacitively coupled RFID tag system. The RFID tag 5b in this alternative RFID tag system includes a dipole antenna connected to the IC chip 6. While the inductively coupled RFID tag system illustrated in FIG. 1 typically operates at a relatively low frequency (from several hundred kHz to several hundred MHz), the capacitively coupled RFID tag system illustrated in FIG. 2 typically operates at a higher frequency (in the 1.0 GHz range or above).

An information transfer process may begin if the RFID tag 5a or 5b is within operative range of the RFID antenna 3. The RFID industry has developed three typical operating ranges: close-coupled, proximity and vicinity. In an information transfer process (reading or programming process), the RFID reader 2 emits an RF field data carrier at a specified frequency to the RFID tag 5a or 5b via its own antenna 3. The specified frequency is typically a data-modulated carrier frequency. The RFID tag antenna is tuned to the same carrier frequency as the reader antenna 3. The RFID tag 5a or 5b parasitically derives its operating power from the RF field received from the reader 2. The carrier signal generates enough power (only a small amount is necessary) in the RFID tag 5a or 5b to operate its IC chip 6. The carrier frequency signal emitted from the reader 2 via its antenna 3 is also modulated with information. This information can be de-modulated by the RFID tag 5a or 5b. The RFID tag 5a or 5b performs desired operations according to the received information. The desired operations may include reading, writing, transmitting, etc. The operation of "transmitting" from a passive, parasitic RFID tag refers to the RFID tag communicating information back to an RFID reader in response to receiving the RFID reader's field. The RFID tag communicates information back to the RFID reader by modulating the RFID reader's field.

If coupling between an RFID reader and an RFID tag is inductive (such as at 13.56 MHz), any small change of resonant frequency of the RFID tag can be detected by the RFID reader. This is because the distance (e.g., 1 meter or so) compared with the wavelength is very small (i.e., a near field effect). Therefore, if RFID tag tries to send information to the RFID reader, it changes its own (tag) properties so that the RFID reader knows the tag being changed. Then the information is sent back to the RFID reader. In other words, the RFID tag transmits information to the RFID reader by modulating the RFID reader's RF field.

Figure 3:
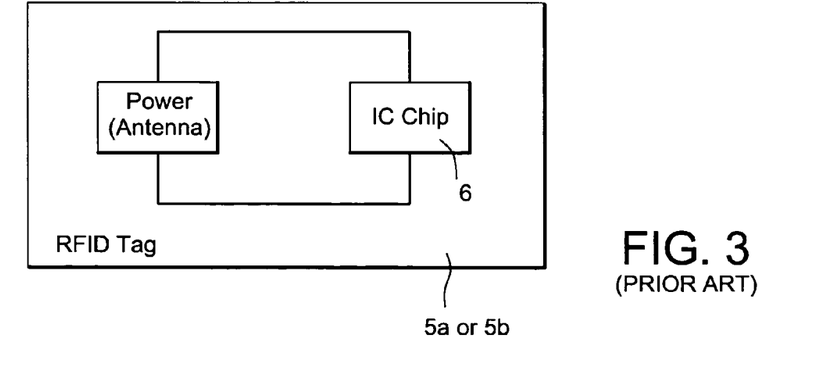
FIG. 3 is a schematic diagram of an equivalent circuit of an RFID tag illustrated in FIG. 1 or 2.

FIG. 3 shows an equivalent circuit of the RFID tag when its IC chip 6 is powered. The power absorbed by the RFID tag antenna effectively acts as a battery providing electrical power to the IC chip. The RF field strength, the orientation of RFID tag antenna in the RF field and the coupling efficiency between the RF field and the RFID tag antenna determines the capacity of the battery.

The emitted RF power of an RFID reader/programmer is typically less than 1 Watt. The peak RF power of an MRI application (e.g., in the imaged volume) frequently exceeds tens of thousands of Watts. A high power RF field, such as that used in an MRI application, may therefore induce a very high voltage and/or current in the RFID tag antenna. This high voltage and/or current may damage or even destroy the IC chip of the RFID tag. A traditional RFID tag thus may not be used in high strength RF field environments such as MRI applications.

SUMMARY

Such problems are solved, in one non-limiting, exemplary embodiment, by an RFID tag for use with an MRI machine, the RFID tag comprising an integrated circuit, and a structure for protecting the integrated circuit from damage or destruction when the RFID tag is exposed to an RF field from the MRI machine.

The structure for protecting the integrated circuit may comprise a controllably low impedance device such as a voltage limiter having two cross-diodes coupled in parallel with the integrated circuit or a series LC resonant circuit coupled in parallel with the integrated circuit. The resonant frequency of the series LC resonant circuit may be at or near the frequency of an RF field from the MRI machine. The controllably low impedance device may alternatively include a tuned transmission line length which is capable of providing a short circuit in parallel with the integrated circuit (or an open circuit in series with the integrated circuit). The transmission line may be, for example, a quarter-wavelength, open-ended transmission line which acts like a short circuit in parallel with the integrated circuit at a frequency of the RF field from the MRI machine. The low impedance device may alternatively include (i) an open-ended transmission line which is less (or more) than a quarter-wavelength long at a frequency of the RF field of the MRI machine to thus act a capacitance (or inductance), and (ii) an inductor (or capacitor) connected in series with the open-ended transmission line, the transmission line and the inductor (or capacitor) forming a series resonant circuit coupled in parallel with the integrated circuit.

The structure for protecting the integrated circuit may also comprise a high impedance device in series with the RFID integrated circuit. The high impedance device may include a recoverable fuse coupled in series with the integrated circuit or a parallel LC resonant circuit coupled in series with the integrated circuit. The resonant frequency of the parallel LC resonant circuit may be a frequency of the RF field from the MRI machine. The high impedance device may alternatively include a quarter-wavelength shorted transmission line which is capable of effectively providing an open circuit in series with the integrated circuit. The high impedance device may alternatively include (i) a shorted transmission line which is less (or more) than a quarter-wavelength long at a frequency of the RF field from the MRI machine to thus act an inductance (or capacitance), and (ii) a capacitor (or inductor) connected in parallel with the shorted transmission line, the transmission line and the capacitor (or inductor) forming a parallel resonant circuit coupled in series with the integrated circuit.

The device for protecting the integrated circuit may comprise an RF filter. The RF filter may comprise a band-pass filter which passes only an RFID reader RF signal. The RF filter may comprise a band-pass filter which blocks signals having a frequency of the MRI machine RF field.

The integrated circuit may include a memory for storing data relating to information or a patient.

The device for protecting the integrated circuit may include two or more of: a low impedance device, a high impedance device, and an RF filter.

In another non-limiting, exemplary embodiment, a system comprises an MRI machine, and at least one RFID tag reader for use in an MRI environment. The at least one RFID tag reader may be disposed to read an RFID tag in a high strength RF field environment of the MRI machine. The MRI machine may include a static magnetic field generator for emitting a static magnetic field into an area which at least partially overlaps with an RFID tag reader RF field. The environment of the MRI machine into which the RFID tag reader is active may at least include an imaging bore or volume defined by the MRI machine. The system may further comprise an RFID tag which communicates with the RFID tag reader when the RFID tag is within the imaging bore (e.g., at a time when the MRI RF fields are not active).

In another non-limiting, exemplary embodiment, a method of operating a system having an MRI machine and at least one RFID tag reader in the MRI environment detects information from at least one RFID tag using the RFID tag reader, processes the detected information, and enables an operation of the MRI machine to be executed only when the processed information indicates that no unwanted article is in the environment of the MRI machine.

In another non-limiting, exemplary embodiment, a method of operating a system having an MRI machine and at least one RFID tag reader in the MRI environment detects information from at least one RFID tag using the RFID tag reader, processes the detected information, and determines whether or not an operation of the MRI machine should be executed based on the processed information. A determination may be made that a particular operation of the MRI machine can be executed if an appropriate part of the MRI system (e.g., the proper RF coil) is present or should not be executed if the processed information indicates the presence of an unwanted article (e.g., the "wrong" RF coil) in the environment of the MRI machine. The unwanted article may include an MRI machine component (e.g., an RF coil) and/or a patient having a particular condition.

In another non-limiting, exemplary embodiment, a method of operating a system having an MRI machine and at least one RFID tag reader detects information from at least one RFID tag using the RFID tag reader, processes the detected information, and enables a certain operation of the MRI machine to begin only if the processed information indicates (a) the presence of necessary components or conditions and/or (b) an absence of any unwanted article in an area in or adjacent to the MRI machine.

In another non-limiting, exemplary embodiment, an RFID tag for use with an MRI machine comprises an integrated circuit, an antenna, coupled to the integrated circuit, for providing electrical power to the integrated circuit, and a device for at least temporarily blocking or reducing electrical power provided to the integrated circuit from the antenna when the RFID tag is exposed to a strong RF field (e.g., from the MRI machine in the imaged volume). The device may comprise a controllably low impedance device coupled in parallel with the integrated circuit. The low impedance device may include two cross-diodes, a series LC resonant circuit, or a transmission line segment, which alone or in series connection with a capacitor or inductor, acts as a series resonant circuit. The device may alternatively or additionally comprise a high impedance device coupled in series with the integrated circuit. The high impedance device may include a recoverable fuse, a parallel LC resonant circuit, or a transmission line segment, which alone or in parallel connection with a capacitor or inductor, acts like a parallel resonant circuit. The device may alternatively or additionally comprise an RF band-pass filter.

BRIEF DESCRIPTION OF THE DRAWINGS

These and other advantages of the exemplary embodiments will be more completely understood and appreciated by careful study of the following more detailed description in conjunction with the accompanying drawings, in which.

DETAILED DESCRIPTION OF NON-LIMITING, EXEMPLARY EMBODIMENTS

Figure 4:
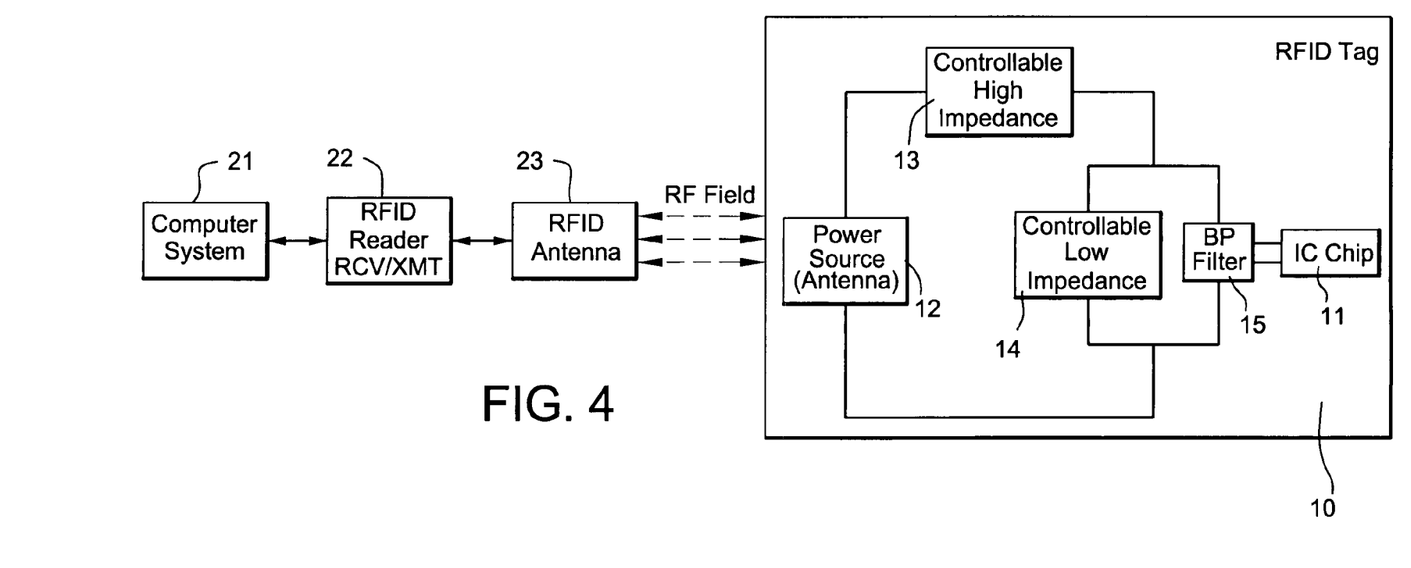
FIG. 4 is a schematic view of an exemplary RFID tag system in accordance with one non-limiting, exemplary embodiment.

FIG. 4 illustrates an exemplary RFID tag system which may be used in accordance with one non-limiting, exemplary embodiment. The RFID tag system includes a computer system 21, an RFID reader 22, an RFID antenna 23 and an RFID tag 10. The computer system 21 may be one of a system of computers which control MRI system functions as will be discussed below. Alternatively, the computer system 21 may be a separate additional computer system which communicates with an MRI system computer. The RFID reader 22 transmits and receives RF fields via its corresponding RFID antenna 23 in order to read information stored in the RFID tag 10. In addition to performing a read function, the RFID reader 22 may optionally be able to perform a programming function. That is, in some cases, it may be beneficial to enable the RFID reader 22 to write or read-modify-write data in a memory of the RFID tag 10. On the other hand, a particular RFID tag system may include an RFID reader 22 having only read capabilities to prevent unauthorized programming of the RFID tag.

The RFID tag includes an IC chip 11 and an antenna 12. The IC chip 11 includes a memory for storing data and executable control instructions. The IC chip 11 executes the control instructions to perform various functions such as retrieving, writing and transmitting data. The data stored in the IC chip 11 may include, for example, patient information such as identification and medical history information and/or information relating to any component of the MRI machine such as device quality assurance information, device history or service record information, device identification information and configuration data. The data stored in the memory of the IC chip 11 may be encrypted via standard techniques to prevent unauthorized tampering.

The antenna 12 may be made of a conductive metal (e.g., copper or aluminium) trace or wire wound in a particular (e.g., circular) pattern. The antenna 12 is tuned to the carrier frequency of the RFID reader 22 via its RFID antenna 23. At this RFID reader frequency ($F_{ID}$), the RFID tag antenna 12 picks up electromagnetic energy from the emitted RF field so that a current is induced in the antenna 12 producing a voltage at its terminals and effectively acting as a battery to provide electrical power to IC chip 11. An exemplary frequency $F_{ID}$ at which the RFID tag antenna 12 and the RFID reader 22 may operate is 13.56 or 24 MHz, although those skilled in the art will appreciate that the RFID tag antenna 12 and the RFID reader 22 may be tuned to operate at other frequencies.

The RFID tag 10 also includes one or more structures for protecting IC chip 11 from a damaging high voltage and/or current when the RFID tag 10 is exposed to a high power RF field. For example, the RFID tag 10 illustrated in FIG. 4 includes a controllably high impedance device 13, a controllably low impedance device 14 and an RF filter 15. While the RFID tag illustrated in FIG. 4 includes three devices for protecting the IC chip 11 from a high amount of electrical power resulting from a high voltage and/or current, those skilled in the art will appreciate that only one or two of the three exemplary devices may be sufficient as illustrated in FIGS. 7-13. The number of such devices for protecting IC chip 11 depends on the amount of protection required. For example, if the highest possible level of protection against high electrical power is needed for the IC chip 11, then all three devices 13-15 may be included in the RFID tag. If the level of protection needed for the IC chip 11 is lower, then a single protection device 13, 14 or 15 may be sufficient.

The controllable high impedance device 13, controllable low impedance device 14 and the RF band-pass filter 15 are each capable of protecting the RFID tag antenna so that a reduced voltage and/or current is applied to the IC chip 11 when it is in the presence of high RF power. However, the protection devices permit normal operating voltage and current induced via the RF field from the low powered RFID reader 22 to provide electrical power to the IC chip 11 for normal RFID operation. During this normal RFID operation, IC chip 11 may modulate or demodulate the electromagnetic RF carrier field from RFID reader 22 in order to retrieve and/or transmit data from/to RFID reader 22. The data transmitted back to RFID reader 22 may then be communicated to computer system 21.

The controllable high impedance device 13 is connected in series with IC chip 11. The controllable high impedance device 13 may be a broadband device or operable at one or more specific frequencies. The operating frequency may be set to operate at a high power RF field frequency which is equal, for example, to a frequency $F_0$ of an MRI RF field. The high impedance device 13 may thus present a high impedance to a signal if, for example, a voltage and/or current limit is exceeded or a field having a particular frequency $F_0$ is received by antenna 12. The high impedance device will reduce the high voltage and/or current presented to the IC chip 11.

The controllable low impedance device 14 is connected in parallel with IC chip 11. The low impedance device 14 may be a broadband device or operable at one or more specific frequencies. The low impedance device 14 may be operable to provide a short circuit across the IC chip 11 so that voltage applied across IC chip 11 will be limited to below a certain threshold. Alternatively, the low impedance device may provide a short circuit across the IC chip 11 when a signal at a specific frequency (e.g., a frequency $F_0$ of an MRI RF field) is received by RFID tag antenna 12.

The RF filter 15 is connected between the antenna 12 and the IC chip 11. The RF filter 15 may allow only a signal having a particular frequency (e.g., the RFID operating frequency $F_{ID}$) to pass to the IC chip 11. That is, the RF filter 15 may be implemented by a band-pass filter between the antenna 12 and the IC chip 11 so that only a signal at frequency $F_{ID}$ passes to the IC chip 11. Other signals having a different frequency (including those having a frequency $F_0$ associated with an MRI application) are effectively blocked by a lower parallel impedance (i.e., this is a species of the controllable low impedance device 14).

Figure 5:
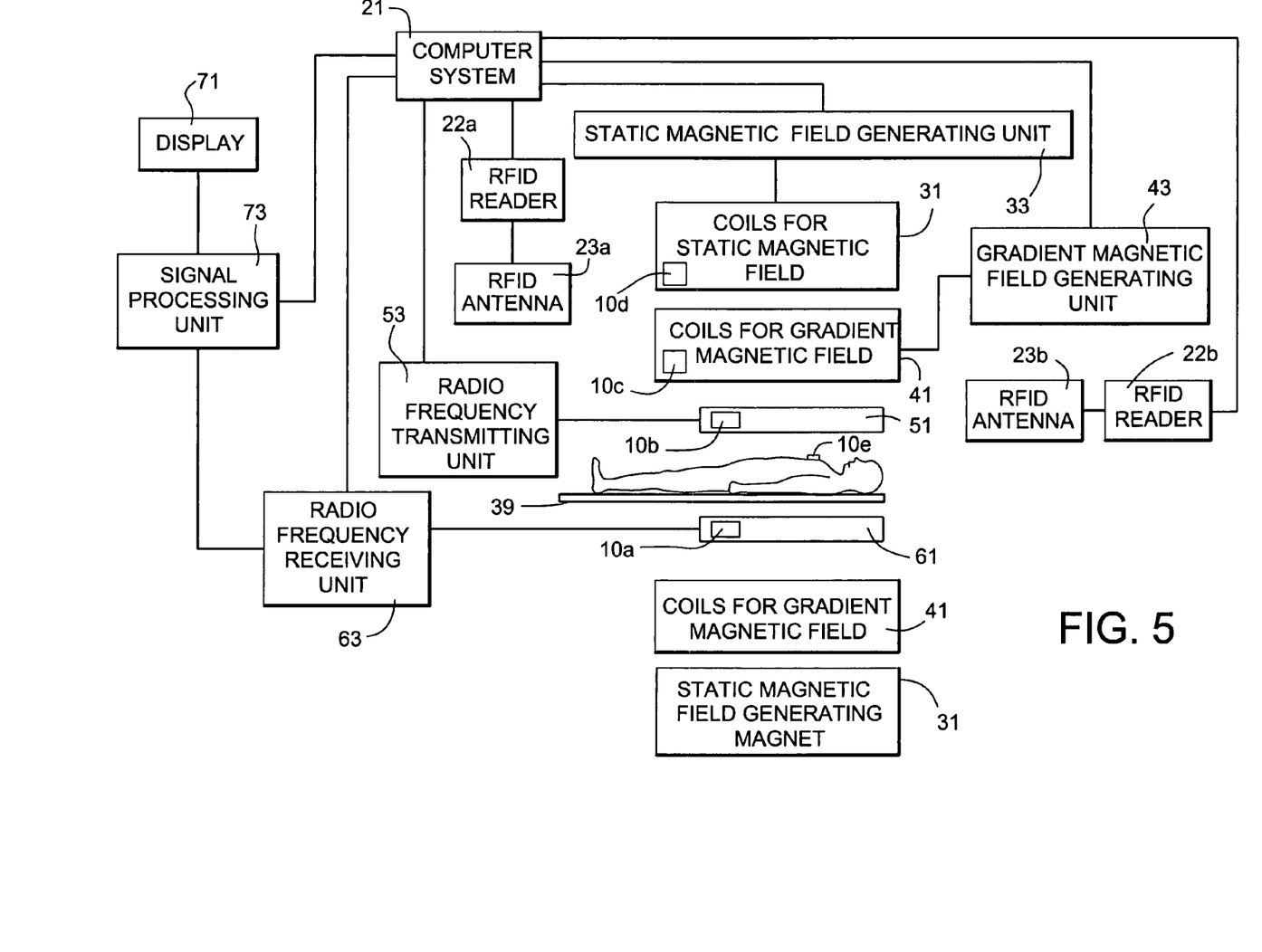
FIG. 5 is an overall system-wide schematic view of an exemplary system incorporating a magnetic resonance imaging (MRI) machine and an RFID tag system in accordance with one non-limiting, exemplary embodiment.

FIG. 5 is a general overview of major components of an exemplary system including an MRI machine and an RFID tag system. The RFID tag system in this exemplary system may be implemented by the RFID tag system illustrated in FIG. 4. The MRI system includes static magnetic field coils 5 31, gradient magnetic field coils 41, an RF transmitting coil 51 (or an array of RF transmitting coils) and RF receiving coils 61. A computer system 21 controls gradient magnetic field coils 41, RF transmitting coil 51 and RF receiving coils 61 through respective units 43, 53 and 63 (and may in some circumstances have some control associated with static magnetic field coils 31 via unit 33). The computer system 21 also communicates with signal processing unit 73 which is capable of generating a display resulting from an MRI application on display 71.

The static magnetic field coils 31 generate a powerful (e.g., 0.5 T, 1.5 T or 3.0 T) uniform magnetic field. The gradient magnetic field coils 41 emit gradient magnetic fields in three orthogonal directions upon receiving appropriate outputs from gradient magnetic field generating unit 43. An RF transmitting coil emits an RF field through operation of the radio frequency transmitting unit 53 to excite nuclei of patient tissue to NMR in the imaged volume. The frequency of the RF field emitted from the RF transmitting coil 51 may have a frequency $F_0$ equal to, for example, 63.6 MHz or 127 MHz. The particular frequency $F_0$ used is determined in large part by the strength of the static uniform magnetic field but cannot equal $F_{ID}$. RF receiving coils 61 receive RF NMR response signals from NMR patient tissue nuclei. The signal processing unit 73 utilizes the received NMR RF signals to generate an image to be displayed on display 71.

In addition to the MRI machine, the system illustrated in FIG. 5 includes an implementation of the RFID tag system illustrated in FIG. 4. In particular, the system includes two RFID readers 22a, 22b each having a respective RFID antenna 23a, 23b. Each of the RFID readers 22a, 22b are connected to computer system 21. While the system illustrated in FIG. 5 includes two RFID readers 22a, 22b, those of ordinary skill in the art will understand that only one or more than two RFID readers can be utilized depending on the extent of the RFID operating range needed. The RFID detection range needed may merely overlap with the MRI imaging tunnel (approximately 1.2 meters in length) in which MRI imaging typically occurs or may extend into the entire gantry room housing the MRI machine. The later case would likely require additional RFID tag readers disposed about the room as desired.

The RFID readers 22a, 22b each operate in an RF field environment of the MRI system (e.g., each being directed into the MRI tunnel from a respectively associated tunnel end) to read information from (and/or optionally write or read-modify-write information into) one or more of the RFID tags 10a-10e. The RFID tags 10a-10f may be attached to one or more components of the MRI system such as, but not limited to the RF transmitting coil 51 and/or the RF receiving coils 61 or other MRI system components as illustrated in FIG. 5. An RFID tag 10e may also be attached to (or within) a patient. As yet another example, an RFID tag may be attached to an operator (not shown) of the system. Any other MRI component or other article within the environment of the MRI machine can be associated with a particular RFID tag. Each of these RFID tags 10a-10e are tuned to the operating frequency $F_{ID}$ of the RFID reader 22a, 22b.

Each of the RFID tags 10a-10e typically may be the size of a standard business card or smaller. Each of the RFID tags 10a-10e may be flexible or may be enclosed by a rigid protective coating as will be appreciated. When attached to an MRI component such as RF coils 51 or 61, the RFID tags 10a-10d will not affect the MRI application (e.g., because it is effectively disabled during MRI operations when high power MRI RF fields are present). The RFID tag 10e associated with the patient may be worn (e.g., wristband), attached to the patient's clothing, or embedded into the patient.

Each of the RFID tags 10a-10d connected to a particular MRI component may store quality assurance control information such as a quality assurance data, revision information, a component control configuration file and/or a service record and the like. The RFID tag 10e coupled to the patient may include the patient's medical history and/or identification information. This information may indicate, for example, what portion of the patient's body should be imaged and/or whether the patient suffers from any condition (e.g., metal implant or claustrophobia) which should prevent the MRI imaging process from even beginning. Through an information transfer process with the RFID tag 10e, hand-entry of patient information by the MRI system operator may be reduced or avoided, thereby minimizing any chance for error.

Figure 6:
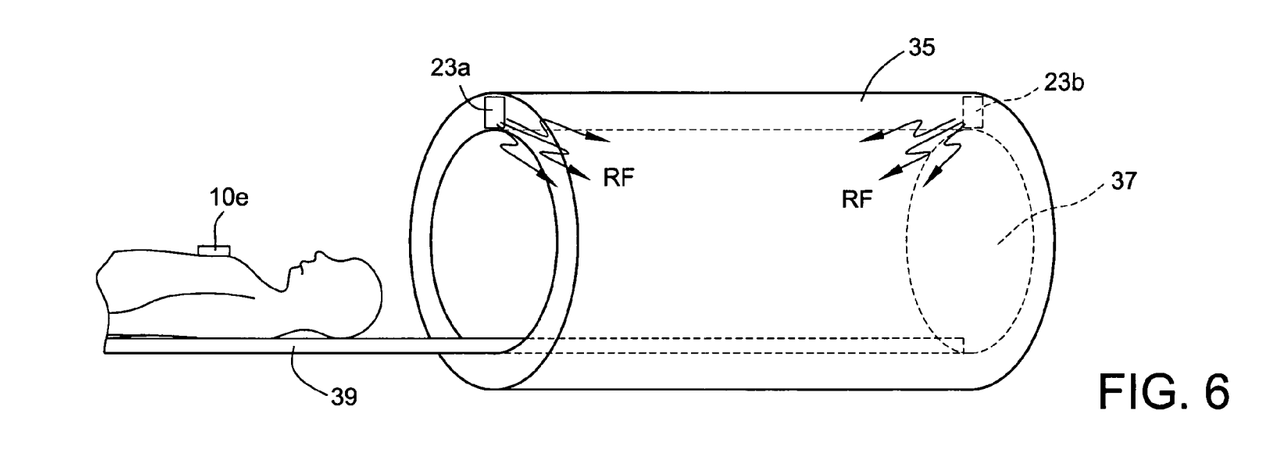
FIG. 6 is an exemplary diagram showing, for example, an imaging bore of the MRI machine illustrated in FIG. 5.

FIG. 6 shows one exemplary implementation of certain components of the system illustrated in FIG. 5. In particular, the static magnetic field coils 31 in this embodiment are shaped in a cylindrical form 35. Cylindrical form 35 defines an imaging bore or tunnel 37 into which a patient may be slid via table 39. RFID antennas 23a and 23b are attached to a portion of cylindrical form 35. These antennas 23a, 23b may be fixedly attached to the cylindrical form 35 or removably attached via appropriate fastening mechanisms such as fastening hooks and/or velcro fasteners (not shown).

The volumes into which the RFID antennas 23a and 23b are effective define the RFID detection range. When an RFID tag is within the detection range, effective communication with the RFID tag and the RFID reader may be accomplished. Here the RFID detection range extends into a high RF field environment of the MRI system. The environment of the MRI system may include three-dimensional areas in and adjacent to any portion of the MRI system. As noted above, however, a larger RFID detection range may require additional RFID readers. On the other hand, the RFID detection range may be specifically focussed to include only the imaging area defined by bore 37 (where the highest intensity RF fields are located) and areas nearby. In this example, the RFID detection range would overlap with the static magnetic, gradient magnetic and RF fields of the MRI machine. As another example, the RFID tag 10e attached to the patient may be within the bore 37 for imaging (see FIG. 5) or outside of the bore 37 (see FIG. 6). In this example, the RFID detection zone would need to include areas inside and outside of the imaging bore 37 to provide communication with the RFID tag 10e in both areas.

The RFID tags 10a-10e, or any other RFID tag in the environment of the MRI system, may be exposed to a high power RF field produced by the MRI machine during its operation. As noted above, such exposure to high power RF fields may cause excessive high voltage and/or current to be applied to an IC chip of the RFID tag to damage or even destroy it. Each of the RFID tags 10a-10e therefore includes at least one of a high impedance device 13, low impedance device 14 and/or RF filter 15 to reduce or altogether block the high voltage and/or current from being applied to the IC chip 6 of the RFID tag 10a-10e. The IC chip 6 in each RFID tag 10a-10e is therefore protected from damage or destruction resulting from excessive application of electrical power even when exposed to high power RF fields associated with MRI applications.

FIGS. 7-13 illustrate various alternatives of an RFID tag 10 which may be used in the environment of an MRI system by disabling the RFID tag antenna so that reduced high voltage and/or current is applied to the IC chip of the RFID tag when the RFID tag is exposed to a high power RF field(s) such as one produced in an MRI application, thereby protecting it from damage or destruction.

Figure 7:
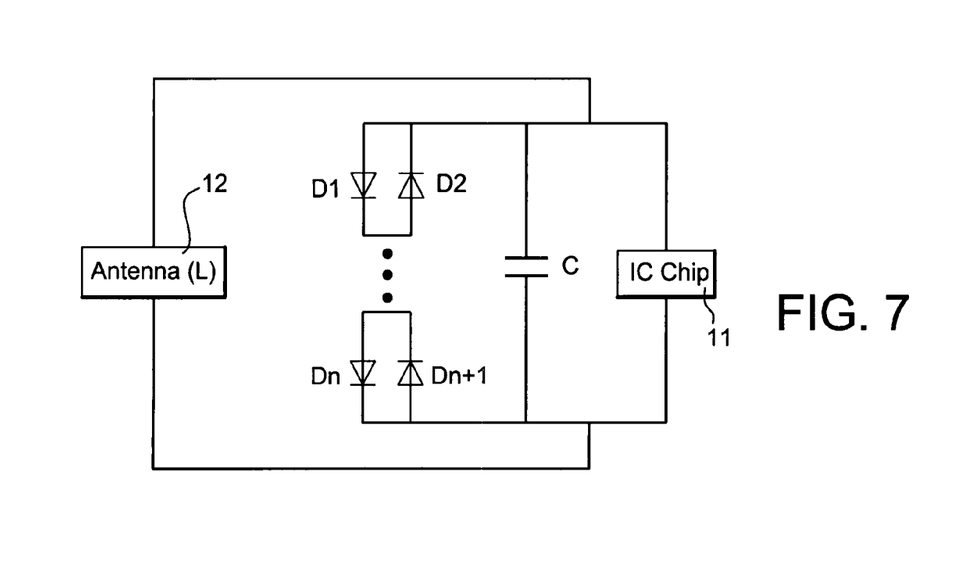
FIG. 7 is an exemplary schematic diagram of an RFID tag which may be used in the system illustrated in FIGS. 4-6 and which includes a broadband, low impedance device.

FIG. 7 shows an example RFID tag which may be utilized in the system illustrated in FIGS. 4-6. The RFID tag includes an IC chip 11, an antenna 12 and a capacitance C for tuning the antenna 12 to the frequency $F_{ID}$ of the RFID reader. The RFID tag also includes a controllable low impedance device connected in parallel with the IC chip 11. In this example, the low impedance device includes multiple pairs of cross-diodes D1, D2-Dn, Dn+1 forming a voltage limiter. The limiting voltage of the voltage limiter determines the maximum voltage which can be applied to the IC chip 11. This limiting voltage of the voltage limiter is set to be higher than the working voltage of the IC chip 11, but lower than the maximum voltage allowed by the IC chip 11.

Diodes D1-Dn+1 may be implemented by, for example, fast switching diodes. Examples of these fast switching diodes may include model nos. 1N6639US-1N6641US produced by Microsemi.

The low impedance device formed by the multiple pairs of cross-diodes D1, D2-Dn, Dn+1 is a broadband protection device. This low impedance device therefore not only works at a particular frequency such as frequency $F_0$ associated with an MRI application, but also works at other frequencies (e.g. all frequencies encountered in the MRI environment) so long as the RF field power is strong enough to switch "on" a cross diode D1, D2, Dn or Dn+1 of the voltage limiter. As an example, a typical maximum voltage which may be applied to an IC chip without damage or destruction is 10 volts. An RF field power of, for example, 50 μT B field or 200K V/meter E field may be strong enough to induce more than 10 volts in the RFID tag. MRI machines typically produce RF fields of this magnitude or greater during operation.

Figure 8:
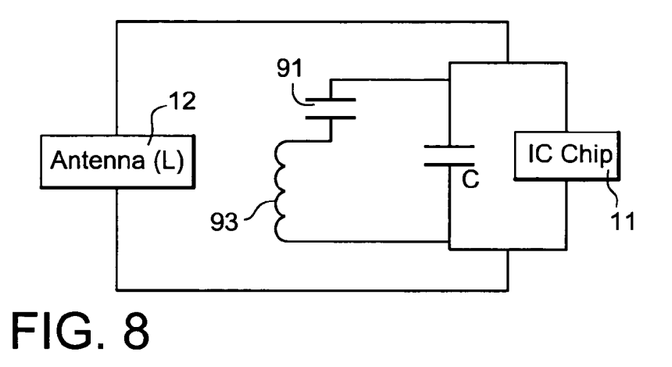
FIG. 8 is an exemplary schematic diagram of an RFID tag which may be used in the system illustrated in FIGS. 4-6 and which includes a frequency-specific, low impedance device.

FIG. 8 illustrates an alternative example RFID tag which may be utilized in the system illustrated in FIGS. 4-6. The RFID tag includes an IC chip 11, an antenna 12 and a capacitance C. The RFID tag also includes a controllable low impedance device connected in parallel with the IC chip 11. The low impedance device is implemented in this alternative embodiment by a series LC resonant circuit. The series LC resonant circuit includes capacitor 91 and inductor 93.

The values of capacitor 91 and inductor 93 may be set so that the series LC circuit has a resonant frequency at a particular frequency such as the frequency $F_0$ of an MRI application. If the RFID tag is exposed to a field having this particular frequency $F_0$, the series LC resonant circuit will create a short circuit across IC chip 11. This short circuit protects the IC chip 11 from being exposed to a high voltage otherwise induced when the RFID tag is exposed to a field having the frequency $F_0$.

While the series LC circuit forming the low impedance device thus creates a short circuit at one frequency (e.g., frequency $F_0$), the IC chip 11 still receives normal electric power from the antenna 12 at another frequency such as frequency $F_{ID}$—the frequency of the RFID reader. That is, while the RFID tag is disabled at frequency $F_0$ for protection purposes, the RFID tag works at frequency $F_{ID}$. The capacitance C is selected such that the reactance of inductor 93 and capacitor 91 in series plus the capacitance C provide parallel resonance with antenna (L) 12 at frequency $F_{ID}$.

In contrast to the RFID tag illustrated in FIG. 7, the controllable low impedance device including the series LC resonant circuit as illustrated in FIG. 8 operates at a specific frequency. That is, the series LC resonant circuit is not a broadband device. Also, the low impedance device including the series LC resonant circuit may be more robust than the low impedance device implemented by cross-diodes/voltage limiter as illustrated in FIG. 7 since the capacitor 91 and inductor 93 may provide superior power handling.

Figure 9:
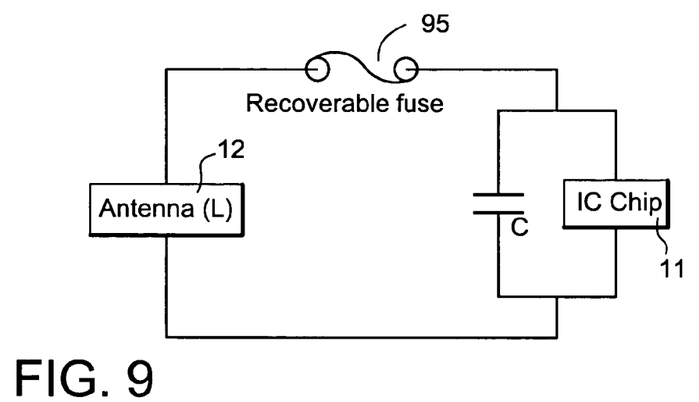
FIG. 9 is an exemplary schematic diagram of an RFID tag which may be used in the system illustrated in FIGS. 4-6 and which includes a broadband, high impedance device.

FIG. 9 illustrates another alternative example RFID tag which may be utilized in the system illustrated in FIGS. 4-6. The RFID tag includes IC chip 11, antenna 12 and capacitance C. The RFID tag also includes a broadband, high impedance device for protecting the IC chip 11. The high impedance device is connected in series with the IC chip 11 and is implemented in this embodiment by a resettable or recoverable device such as an auto-recoverable fuse 95. The fuse 95 possesses a fuse limit which is larger than the IC chip working current condition, but smaller than its maximum allowable current condition. Exposure of the IC chip to a current equal to or greater than its maximum condition may damage or even destroy the IC chip.

When the RFID tag is placed into a high power RF field (e.g., 50 μT B field or 200K V/meter E field), an induced RF current will temporarily open the fuse 50 and thus protect the IC chip 11. Since fuse 95 is recoverable, it returns to a closed condition after the RFID tag leaves regions of the high power RF field. For example, fuse 95 will be automatically recovered after leaving the MRI system environment having high power RF fields. One example of a resettable or recoverable device which may be utilized in this embodiment is manufactured by Digi-Key.

The fuse 95 is a broadband device and thus is capable of opening from a signal of any frequency so long as the induced current level is high enough. However, since fuse 95 presents operating resistance losses, it may decrease the quality factor of the RFID tag antenna 12. As a result, the effective detection range of the RFID reader may be more limited than otherwise.

Figure 10:
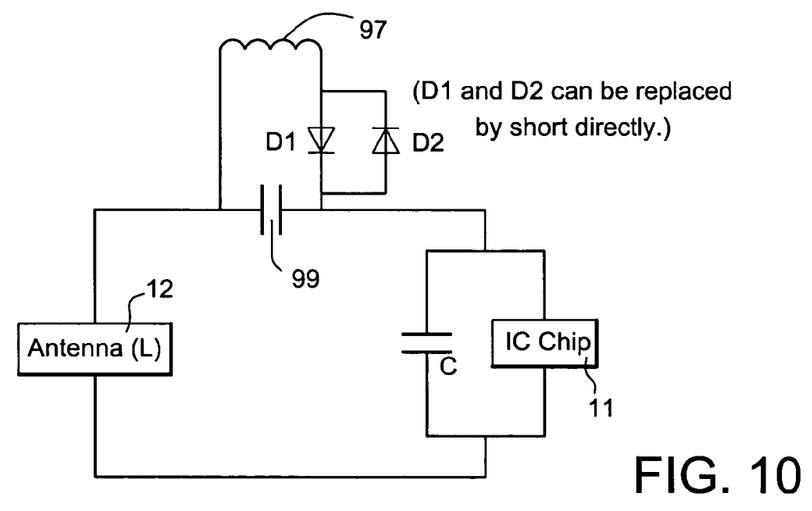
FIG. 10 is an exemplary schematic diagram of an RFID tag which may be used in the system illustrated in FIGS. 4-6 and which includes a frequency-specific, high impedance device.

FIG. 10 illustrates another alternative example RFID tag which may be used in the system illustrated in FIGS. 4-6. The RFID tag includes IC chip 11, antenna 12 and capacitance C. The RFID tag also includes a frequency-specific, controllable high impedance device for protecting IC chip 11. The high impedance device is connected in series with IC chip 11 and includes a parallel LC resonant circuit having an inductor 97 and a capacitor 99. The parallel LC resonant circuit may also include two cross-diodes D1 and D2 as illustrated in FIG. 10. However, these cross-diodes D1-D2 may be replaced by a short circuit to improve block impedance.

The values of inductor 97 and capacitor 99 are selected so that the parallel LC circuit resonates at a particular frequency, such as the RF field frequency $F_0$ of an MRI application. The parallel LC circuit therefore presents a high impedance (e.g., effectively acts as an open circuit) at frequency $F_0$ so that such a signal is reduced or blocked to thereby protect the IC chip when exposed to a signal having frequency $F_0$.

On the other hand, the parallel LC circuit (including capacitor 99 and inductor 97) does not present such a high impedance for an applied signal having another frequency, such as a signal having frequency $F_{ID}$ of the RFID reader. The value of capacitance C is selected such that capacitance C, inductor 97, capacitor 99 and antenna (L) 12 resonate in parallel mode at frequency $F_{ID}$. Unlike the high impedance device illustrated in the RFID tag of FIG. 9, the high impedance device implemented by the parallel resonant LC circuit does not provide a particularly broadband protection scheme for the IC chip 11.

Figure 11:
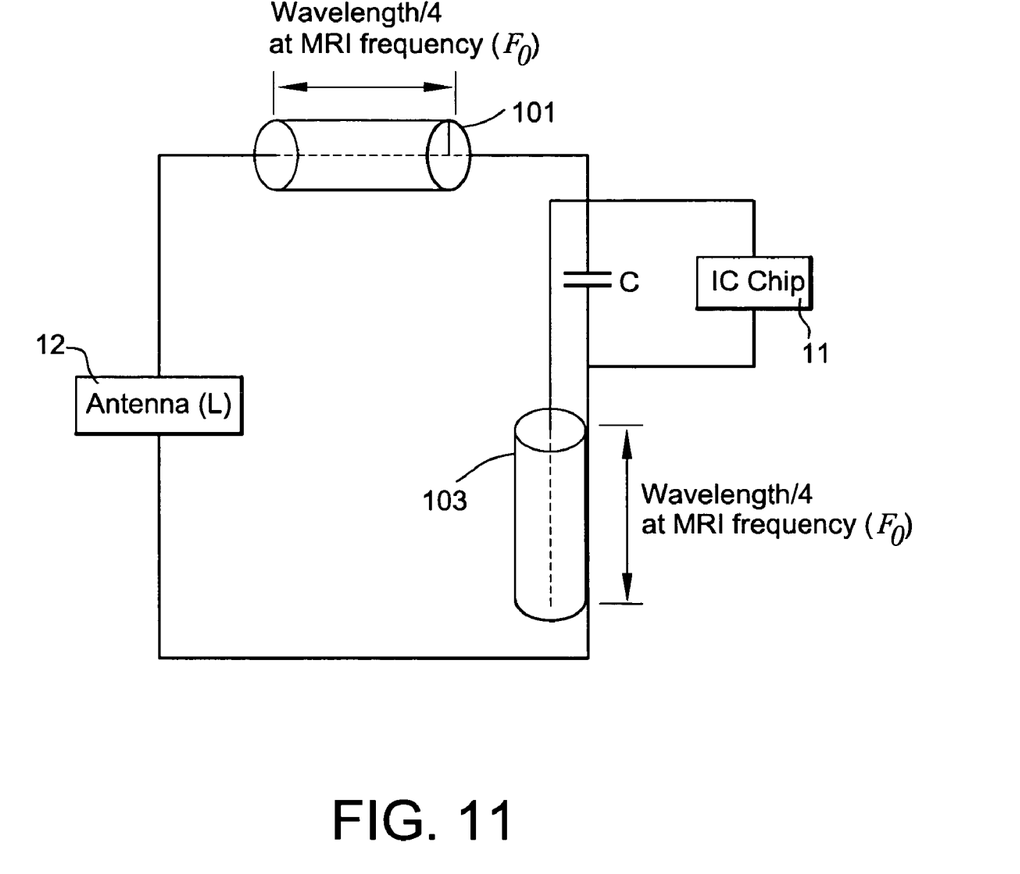
FIG. 11 is an exemplary schematic diagram of an RFID tag which may be used in the system illustrated in FIGS. 4-6 and which includes high and low impedance devices implemented by quarter-wavelength transmission lines.

FIG. 11 shows another alternative example RFID tag which may be utilized in the system illustrated in FIGS. 4-6. The RFID tag includes IC chip 11, antenna 12 and capacitance C. The RFID tag also includes two quarter-wavelength transmission lines 101 and 103. The transmission line 101 is connected in series with the IC chip 11 and the transmission line 103 is connected in parallel with the IC chip 11. The transmission line 101 is shorted at one end. That is, one side (the right side illustrated in FIG. 11) of the transmission line 101 is shorted as the center wire is connected to the shield. In contrast, the transmission line 103 is open at its end. For example, transmission line 103 is not shorted at its bottom side illustrated in FIG. 11. While the embodiment illustrated in FIG. 11 includes two transmission lines 101 and 103, those skilled in the art will understand that only one may be required if a lesser amount of protection is needed for IC chip 11. Each of the transmission lines may be implemented by a PCB compatible transmission line (e.g., a microstrip, strip line, etc.).

Each of the transmission lines 101 and 103 is at a quarter-wavelength at a particular applied frequency, such as, in this example, RF field frequency $F_0$ of an MRI application. Each of these transmission lines thus acts as a resonant circuit at this particular frequency $F_0$. Since the output end of the transmission line 101 is short circuited, the transmission line 101 will act like a high-impedance device (e.g., a parallel resonant circuit) at the frequency $F_0$. That is, the input end (left side in FIG. 11) of the transmission line 101 acts like an open circuit at frequency $F_0$. This high impedance circuit will reduce or block the signal at frequency $F_0$, thereby protecting IC chip.

On the other hand, since the output end (bottom end illustrated in FIG. 11) of the transmission line 103 is open, transmission line 103 will act as a low impedance device (e.g., a series resonant circuit) at frequency $F_0$. As described above in the embodiment of FIG. 9 having a series resonant circuit, a short circuit will be formed across IC chip 11 at frequency $F_0$, thereby protecting the IC chip 11 from receiving excessive voltage and/or current which may damage or destroy it. That is, the input side (top side illustrated in FIG. 11) of the transmission line 103 acts like a short circuit at frequency $F_0$.

The value of capacitor C is selected so that capacitor C, the reactance from transmission line 101, the reactance from transmission line 103 and the antenna (L) 12 resonate in parallel mode at a particular frequency such as the frequency $F_{ID}$ of the RFID reader. Accordingly, the RFID tag illustrated in FIG. 11 still operates properly when the RFID tag is exposed to an RF field emitted from the RFID reader. The transmission line 101 does not block a signal at frequency $F_{ID}$ and the transmission line 103 does not short out a signal having frequency $F_{ID}$.

Handling the capacitors, inductors, diodes and fuses in the embodiments of the RFID tag illustrated in FIGS. 7-10 may be cumbersome. Implementation of these circuit elements may also require additional soldering. Use of transmission lines as illustrated in the embodiment of FIG. 11 may therefore improve manufacturability. In particular, manufacturing of the RFID tag may be more easily automated.

Figure 12:
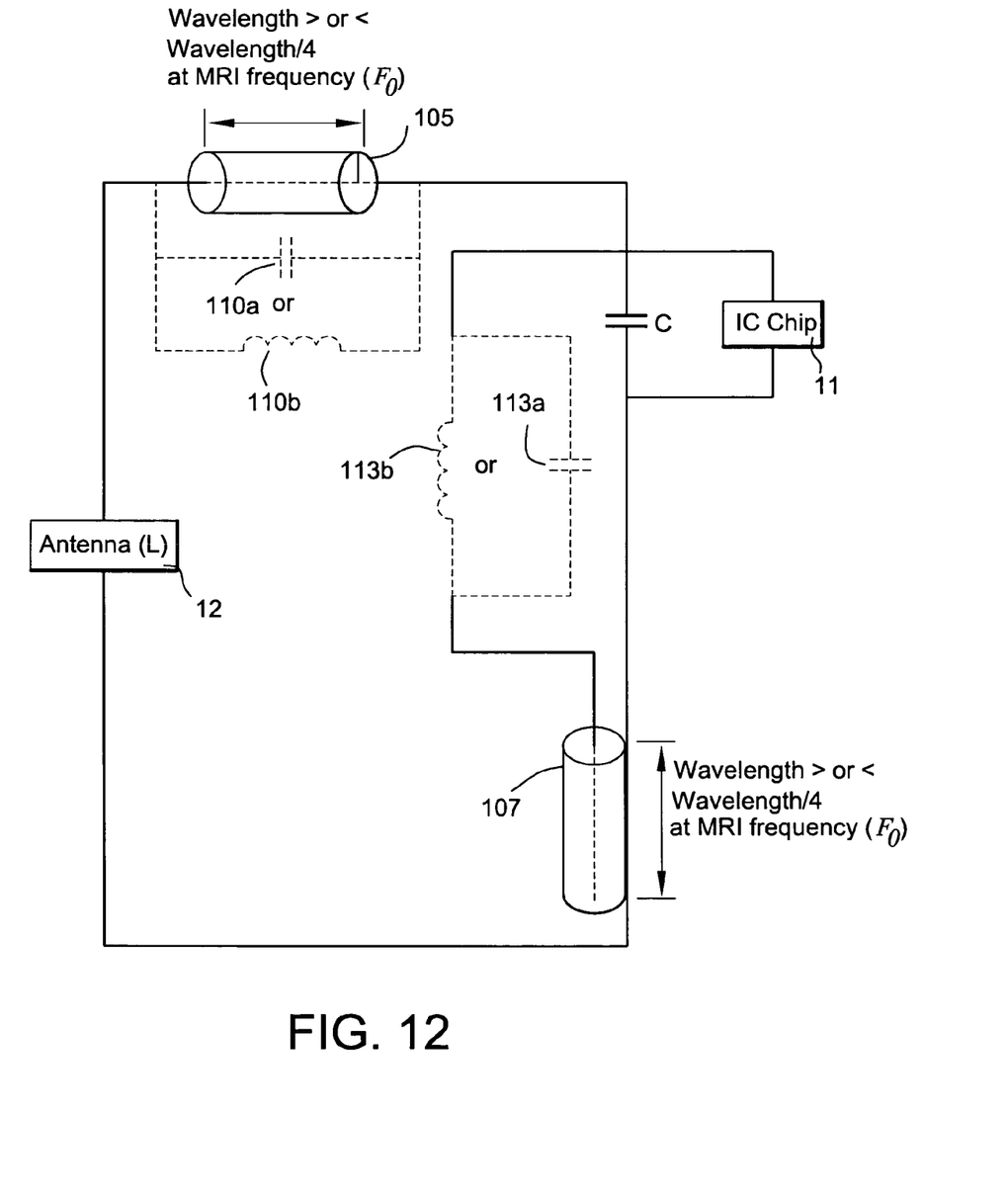
FIG. 12 is an exemplary schematic diagram of an RFID tag which may be used in the system illustrated in FIGS. 4-6 and which includes high and low impedance devices implemented using respective transmission lines.

FIG. 12 illustrates another alternative example RFID tag which may be utilized in the system illustrated in FIGS. 4-6. Similar to the example embodiment illustrated in FIG. 11, the RFID tag illustrated in FIG. 12 includes two transmission lines 105 and 107. However, one or more of the transmission lines 105 and 107 are not a quarter-wavelength at the frequency $F_0$ of the MRI application.

The shorted transmission line 105 may act as a capacitance or an inductance. In particular, if shorted transmission line 105 is less than ¼ wavelength long (or ½ to ¾ wavelength) at frequency $F_0$, the transmission line 105 would act as an inductance. Since the transmission line 105 acts as an inductance when it is less than a quarter-wavelength long, a capacitance 110a can be connected in parallel with the transmission line 105 in order to form a parallel resonant circuit. This parallel resonant circuit, similar to the parallel resonant circuit described in the embodiment of FIG. 10, will reduce or block at signal at frequency $F_0$, thereby protecting the IC chip 11. The parallel resonant circuit will not reduce or block a signal having a different frequency such as frequency $F_{ID}$.

On the other hand, if the shorted transmission line 105 has a length of ¼ to ½ wavelength (or ¾ to 1 wavelength) at the frequency $F_0$, the transmission line 105 will act as a capacitance. In this case, an inductor 110b can be connected in parallel with the transmission line 105 to thus effectively again create a parallel resonant circuit. The value of the inductor 110b and transmission line length can be selected so that the parallel circuit has a resonant frequency at frequency $F_0$. This parallel resonant circuit will act as a high impedance device to reduce or block signals having a frequency $F_0$, thereby protecting the IC chip 11.

The open-ended transmission line 107 may also act as a capacitance or an inductance. In particular, if the open-ended transmission line 107 is less than a quarter-wavelength long (or ½ to ¾ wavelength) at frequency $F_0$, the transmission line 107 will act as a capacitance. Since the transmission line 107 acts as a capacitance, it can be serially connected to inductor 113b to thereby form a series LC circuit. The value of the inductor 113b and length of transmission line 107 may be selected so that the effective series LC circuit resonates at a particular frequency such as RF frequency $F_0$ of an MRI application. At this frequency $F_0$, the series LC resonant circuit will act as a low impedance device (e.g., act as a short-circuit) to thereby protect IC chip 11 in a manner similar to that discussed in connection with the embodiment of FIG. 8.

On the other hand, if the open-ended transmission line 107 is ¼ to ½ wavelengths or ¾ to 1 wavelength long at frequency $F_0$, it will act as an inductance. In this case, transmission line 107 can be connected to capacitor 113a to effectively form a series LC circuit. Inductor and transmission line length values are chosen so that the effective LC circuit resonates at frequency $F_0$. Again, a low impedance device (e.g., short circuit) is formed in parallel with the IC chip 11, thereby protecting it from high power RF signals which may damage or destroy it. However, signals at other frequencies such as frequency $F_{ID}$ will not be shorted by the series LC resonant circuit.

In another alternative embodiment, the shorted transmission line 105 may be replaced by an open-ended transmission line. As discussed above, an open-ended transmission line will act as a capacitance (or inductance) if it is less (or greater) than a quarter-wavelength long at frequency $F_0$. When acting as a capacitance (or inductance), the transmission line can be connected to inductor 110b (or capacitor 110a) to form a parallel resonant circuit. In another alternative embodiment, open-ended transmission line 107 may be replaced by a shorted transmission line. As discussed above, a shorted transmission line will act as an inductance (or capacitance) if it is less (or greater) than a quarter-wavelength long at frequency $F_0$. When acting as an inductance (or capacitance), the open-ended transmission line may be connected to capacitor 113a (or inductor 113b) to form a series resonant circuit.

Figure 13:
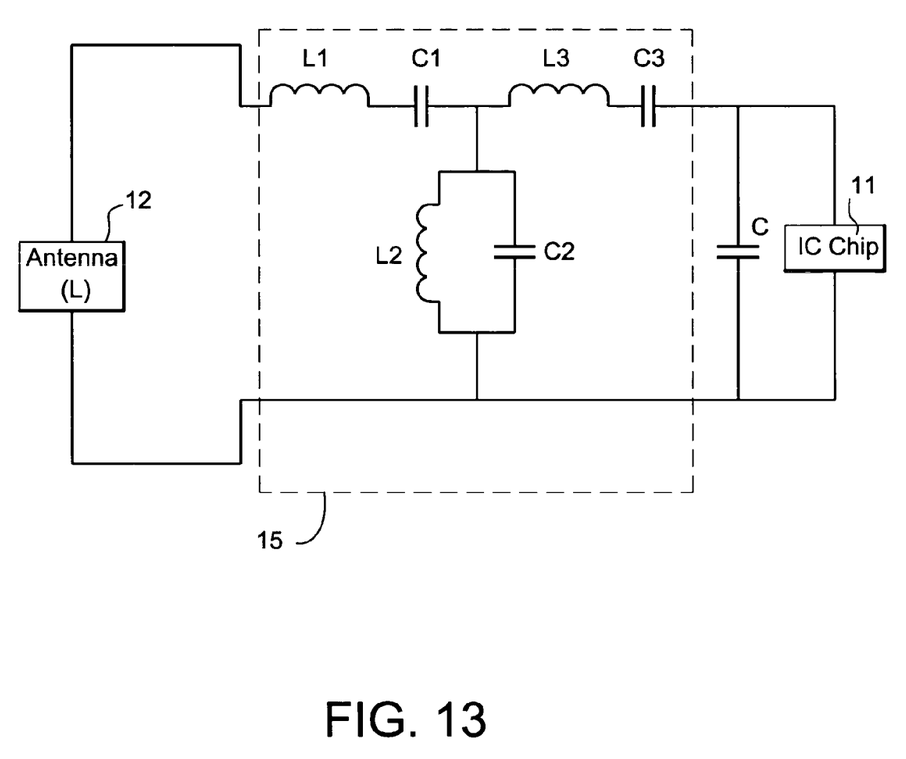
FIG. 13 is an exemplary schematic diagram of an RFID tag which may be used in the system illustrated in FIGS. 4-6 and which includes an RF filter.

FIG. 13 illustrates another alternative example RFID tag which may be utilized in the system illustrated in FIGS. 4-6. The RFID tag includes IC chip 11, antenna 12 and capacitance C. The RFID tag also includes an RF band-pass filter 15. The band-pass filter illustrated in FIG. 13 includes inductors L1-L3 and capacitors C1-C3 to include impedance matching sections at each end. However, those skilled in the art will understand that other configurations for implementing a band-pass filter are possible. The values of the inductors L1-L3 and capacitors C1-C3 are selected so that the bandpass filter passes only a signal having a particular frequency such as frequency $F_{ID}$. Other frequencies such as frequency $F_O$ of an MRI application are not passed, thereby protecting the IC chip 11.

Figure 14:
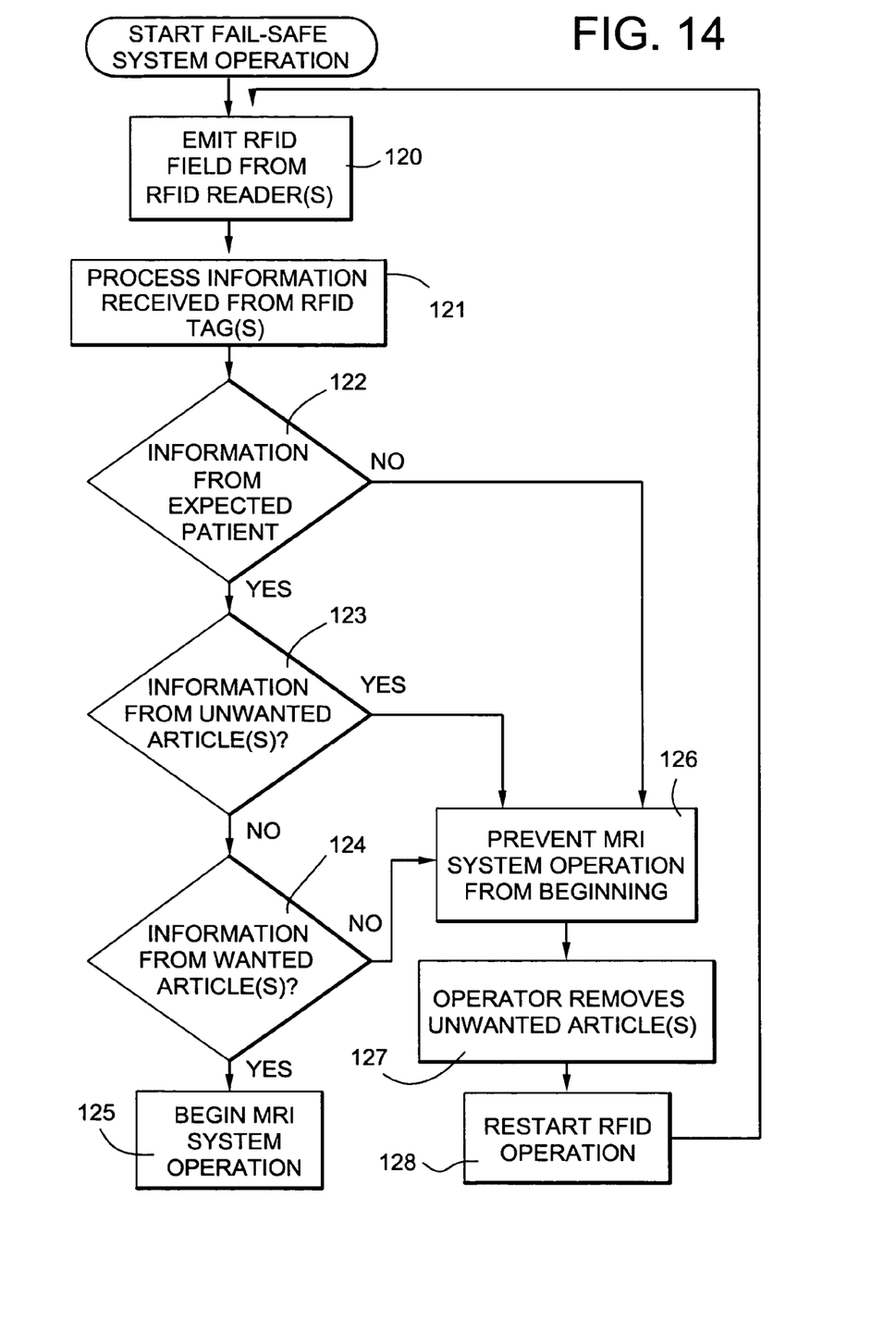
FIG. 14 is an abbreviated schematic flowchart illustrating an exemplary method of operating the system illustrated in FIGS. 4-6.

FIG. 14 illustrates a non-limiting exemplary process which may be performed using the system illustrated in FIGS. 4-6. Through this process, the presence of any unwanted (or wanted) article(s) in the environment of the MRI machine (e.g., in or anywhere near the MRI machine) can be detected. These unwanted (or wanted) articles may be, for example, MRI components or other devices which interfere with (or facilitate or permit) proper MRI machine operation or which can be damaged by the high RF power fields produced by the MRI machine. The unwanted article may also include a patient having a medical condition (e.g., metal implant or claustrophobia) which indicates that the patient would not be a good candidate for an MRI scan.

Before each MRI scanning sequence, one or more RFID readers will "read" the environment of the MRI machine (step 120). The detection range of the RFID readers may be set to cover the entire MRI imaging bore and/or its nearby area. The number of RFID readers may be increased to increase the RFID detection range or volume to cover, for example, the entire room housing the MRI system or just the imaging tunnel. The computer system 21 then processes any information received from the RFID tag(s) present in the environment of the MRI system (step 121). If no information is received, this may itself serve as an error message if RFID tags are known to be or supposed to be within the MRI machine environment.

The computer system 21 determines, based on the processed information from the RFID tag(s), whether any unwanted (or wanted) articles are in the MRI machine environment (step 123). For example, an operator of a previous MRI scan may have erroneously left an unconnected MRI RF coil or other component within the MRI imaging bore. The presence of these unplugged and unused MRI components would not be detected by a traditional MRI system and thus the MRI machine and/or the unplugged coil may be damaged during a subsequent MRI scan. However, if this unwanted MRI component were tagged with an RFID tag, its presence could be detected by the RFID tag reader system in steps 120-121. Alternatively, a certain set or subset of MRI sequences may only be suitable if a certain RF coil is present and used. Thus, computer system 21 may selectively permit only the appropriate MRI sequence to be used.

If no unwanted article(s) are detected in the MRI system environment ("NO" in step 123), MRI machine operation may begin (step 125), or if the MRI system operation has already begun, it may be continued without a danger of damaging an unwanted article and/or the MRI machine itself. If there is an unwanted article in the MRI environment ("YES" in step 123), then the computer system 21 may automatically prevent the MRI machine from beginning to operate (e.g., prevent the MRI system from beginning another scan) (step 126). If MRI operation has already begun, the computer system 21 may automatically and immediately stop the operation to minimize any potential damage to the unwanted article and/or MRI system. The system operator may then remove the unwanted article(s) (step 127), and then restart RFID operation (step 128) or the MRI scan. As also depicted, RFID may be used to insure that the proper patient (step 122) and/or proper MRI system components are present (step 124) before permitting MRI system operations.

The process described in FIG. 14 may thus provide a more fail-safe system operation so that an MRI application may begin only if no unwanted article is found (and/or all wanted articles and patient are found) in the MRI machine environment. The computer system 21 will not permit the MRI scan from even beginning if an unwanted article is detected (or wanted things are not detected). If an MRI scan has already begun and the RFID tag detects the presence of an unwanted article (or absence of a wanted article), the computer system 21 can automatically and immediately stop the MRI operation. The RFID detection of information from RFID tags can thus be performed before or during an MRI scan (e.g., at times when no strong RF fields are present) to determine the presence of unwanted article(s) and stop the MRI scan if necessary.

While the invention has been described in connection with what is presently considered to be practical exemplary embodiments, it is to be understood that the invention is not limited to the disclosed embodiments, but, on the contrary, is intended to cover all variations, modifications and equivalent arrangements included within the spirit and scope of the appended claims.

What is claimed is:

1. An RFID tag for use with an MRI (Magnetic Resonance Imaging) machine, the RFID tag comprising:
   an RFID integrated circuit; and
   structure connected to the RFID integrated circuit to protect it from damage when the RFID tag is exposed to an MRI RF transmitter field while still permitting a signal for operation of the RFID integrated circuit to pass through the structure to the RFID integrated circuit.

2. An RFID tag as in claim 1 wherein said structure comprises a controllable low impedance device.

3. An RFID tag as in claim 2 wherein the controllable low impedance device comprises a voltage limiter having two diodes cross-coupled in parallel with the integrated circuit.

4. An RFID tag as in claim 2 wherein the controllable low impedance device comprises a series LC resonant circuit connected in parallel with the integrated circuit.

5. An RFID tag as in claim 4 wherein a resonant frequency of the series LC resonant circuit is a frequency of the MRI RF transmitter.

6. An RFID tag as in claim 2 wherein the controllable low impedance device comprises a transmission line segment having a length which provides a low impedance in parallel with the integrated circuit at a predetermined MRI RF frequency.

7. An RFID tag as in claim 6 wherein the transmission line is a quarter-wavelength, open transmission line which provides a short circuit in parallel with the integrated circuit at said frequency.

8. An RFID tag as in claim 2 wherein the controllable low impedance device comprises (i) an open transmission line which is less than a quarter-wavelength long at a predetermined MRI RF frequency to thus act a capacitance, and (ii) an inductor connected in series with the open transmission line, the transmission line and the inductor forming a series resonant circuit coupled in parallel with the integrated circuit.

9. An RFID tag as in claim 2 wherein the controllable low impedance device comprises (i) an open transmission line which is more than a quarter-wavelength long at a predetermined MRI RF frequency to thus act a inductance, and (ii) a capacitor connected in series with the open transmission line, the transmission line and the capacitor forming a series resonant circuit coupled in parallel with the integrated circuit.

10. An RFID tag as in claim 1 wherein the structure for protecting the integrated circuit comprises a controllable high impedance device.

11. An RFID tag as in claim 10 wherein the controllable high impedance device comprises a recoverable fuse coupled in series with the integrated circuit.

12. An RFID tag as in claim 10 wherein the controllable high impedance device comprises a parallel LC resonant circuit coupled in series with the integrated circuit.

13. An RFID tag as in claim 12 wherein a resonant frequency of the parallel LC resonant circuit is a predetermined MRI RF frequency.

14. An RFID tag as in claim 10 wherein the controllable high impedance device comprises a short-ended transmission line which is capable of providing an open circuit in series with the integrated circuit.

15. An RFID tag as in claim 14 wherein the transmission line is a quarter-wavelength, shorted transmission line which provides an open circuit in series with the integrated circuit at a predetermined MRI RF frequency.

16. An RFID tag as in claim 10 wherein the controllable high impedance device comprises (i) a shorted transmission line which is less than a quarter-wavelength long at an MRI RF frequency machine to thus act an inductance, and (ii) a capacitor connected in parallel with the shorted transmission line, the transmission line and the capacitor forming a parallel resonant circuit coupled in series with the integrated circuit.

17. An RFID tag as in claim 10 wherein the controllable high impedance device comprises (i) a shorted transmission line which is more than a quarter-wavelength long at an MRI RF frequency to thus act a capacitance, and (ii) an inductor connected in parallel with the short-ended transmission line, the transmission line and the inductor forming a parallel resonant circuit coupled in series with the integrated circuit.

18. An RFID tag as in claim 1 wherein the structure for protecting the integrated circuit comprises a frequency selective RF filter.

19. An RFID tag as in claim 18 wherein the RF filter comprises a band-pass filter which passes only signals having an RFID reader frequency.

20. An RFID tag as in claim 18, wherein the RF filter comprises a band-pass filter which blocks at least an MRI RF frequency.

21. An RFID tag as in claim 1, wherein the integrated circuit includes memory for storing data relating to information about one or more MRI machine components.

22. An RFID tag as in claim 1, wherein the integrated circuit includes memory that stores data relating to patient information.

23. An RFID tag as in claim 1, wherein the structure for protecting the integrated circuit includes two or more of: a controllable low impedance device, a controllable high impedance device, and a frequency selective RF filter.

24. An RFID tag as in claim 2 wherein the controllable low impedance device comprises (i) a shorted transmission line which is less than a quarter-wavelength long at a predetermined MRI RF frequency to thus act a inductance, and (ii) a capacitor connected in series with the shorted transmission line, the transmission line and the capacitor forming a series resonant circuit coupled in parallel with the integrated circuit.

25. An RFID tag as in claim 2 wherein the controllable low impedance device comprises (i) a shorted transmission line which is more than a quarter-wavelength long at a predetermined MRI RF frequency to thus act a capacitance, and (ii) an inductor connected in series with the shorted transmission line, the transmission line and the inductor forming a series resonant circuit coupled in parallel with the integrated circuit.

26. An RFID tag as in claim 10 wherein the controllable high impedance device comprises (i) an open transmission line which is less than a quarter-wavelength long at an MRI RF frequency machine to thus act an capacitance, and (ii) a inductor connected in parallel with the open transmission line, the transmission line and the inductor forming a parallel resonant circuit coupled in series with the integrated circuit.

27. An RFID tag as in claim 10 wherein the controllable high impedance device comprises (i) an open transmission line which is more than a quarter-wavelength long at an MRI RF frequency to thus act a inductance, and (ii) a capacitor connected in parallel with the open transmission line, the transmission line and the capacitor forming a parallel resonant circuit coupled in series with the integrated circuit.

28. A system comprising:
an MRI system; and
at least one RFID tag reader disposed to read an RFID tag while the RFID tag is located in a high strength RF field environment of the MRI system;
wherein the RFID tag includes an integrated circuit and structure for protecting the integrated circuit from damage when the RFID tag is exposed to a strong MRI RF field while still permitting a signal for operation of the integrated circuit of the RFID tag to pass through the structure to the integrated circuit.

29. A system as in claim 28, wherein the MRI system includes a static magnetic field which at least partially overlaps with the reading volume of an RFID tag reader.

30. A system as in claim 28 wherein the RFID tag reader is disposed to read an RFID tag located within an MRI imaging bore.

31. A system as in claim 30 further comprising an RFID tag which communicates with the RFID tag reader within the MRI imaging bore.

32. A system as in claim 28 wherein the structure for protecting the integrated circuit comprises one or more of: a controllable low impedance device coupled in parallel with the integrated circuit, a controllable high impedance device coupled in series with the integrated circuit, and a frequency selective RF filter.

33. An RFID tag for use with an MRI machine, the RFID tag comprising:
an integrated circuit;
an antenna, coupled to the integrated circuit for providing electrical power to the integrated circuit; and
structure at least temporarily reducing electrical power provided to the integrated circuit from the antenna when the RFID tag is exposed to an MRI RF transmitter field while still permitting a signal for operation of the integrated circuit of the RFID tag to pass through the structure to the integrated circuit.

34. An RFID tag as in claim 33 wherein the structure comprises controllable low impedance device coupled in parallel with the integrated circuit.

35. An RFID tag as in claim 34 wherein the controllable low impedance device includes two cross-connected diodes.

36. An RFID tag as in claim 34 wherein the controllable low impedance device includes a series LC resonant circuit.

37. An RFID tag as in claim 34 wherein the controllable low impedance device comprises a transmission line, which alone or in serial connection with a capacitor or inductor, acts as a series resonant circuit.

38. An RFID tag as in claim 33 wherein the structure comprises a controllable high impedance device coupled in series with the integrated circuit.

39. An RFID tag as in claim 38 wherein the controllable high impedance device comprises a recoverable fuse.

40. An RFID tag as in claim 38 wherein the controllable high impedance device comprises a parallel LC resonant circuit.

41. An RFID tag as in claim 38 wherein the controllable high impedance device comprises a transmission line, which alone or in parallel connection with a capacitor or inductor, acts as a parallel resonant circuit.

42. An RFID tag as in claim 33 wherein the structure comprises an RF band-pass filter.

* * * * *